(12) United States Patent
Nozato

(10) Patent No.: US 10,357,155 B2
(45) Date of Patent: Jul. 23, 2019

(54) WAVEFRONT CORRECTION METHOD FOR ADAPTIVE OPTICS SYSTEM

(71) Applicant: CANON KABUSHIKI KAISHA, Tokyo (JP)

(72) Inventor: Koji Nozato, Yokohama (JP)

(73) Assignee: Canon Kabushiki Kaisha, Tokyo (JP)

(*) Notice: Subject to any disclaimer, the term of this patent is extended or adjusted under 35 U.S.C. 154(b) by 0 days.

(21) Appl. No.: 15/795,111

(22) Filed: Oct. 26, 2017

(65) Prior Publication Data

US 2018/0042476 A1  Feb. 15, 2018

Related U.S. Application Data

(63) Continuation of application No. 15/099,435, filed on Apr. 14, 2016, now Pat. No. 9,808,153.

(51) Int. Cl.
| | |
|---|---|
| *A61B 3/12* | (2006.01) |
| *A61B 3/10* | (2006.01) |
| *A61B 3/00* | (2006.01) |
| *G02B 27/09* | (2006.01) |
| *G02B 27/00* | (2006.01) |
| *A61B 3/14* | (2006.01) |

(52) U.S. Cl.
CPC .......... *A61B 3/1225* (2013.01); *A61B 3/0025* (2013.01); *A61B 3/1015* (2013.01); *A61B 3/1025* (2013.01); *A61B 3/14* (2013.01); *G02B 27/0068* (2013.01); *G02B 27/0927* (2013.01)

(58) Field of Classification Search
CPC ....... A61B 3/1225; A61B 3/14; A61B 3/1025; A61B 3/1015; A61B 3/0025; G02B 27/0068; G02B 27/0927
USPC ........................................ 351/200, 205, 221
See application file for complete search history.

(56) References Cited

U.S. PATENT DOCUMENTS

2016/0089016 A1* 3/2016 Shibata ................ A61B 3/0025
351/206

* cited by examiner

*Primary Examiner* — Tuyen Tra
(74) *Attorney, Agent, or Firm* — Canon U.S.A., Inc. IP Division

(57) ABSTRACT

A method, controller, and medium to control an adaptive optics scanning laser ophthalmoscope. Receiving from the ophthalmoscope a plurality of wavefront elements. Each element may be associated with an area of a beam of light received from a fundus. Each element includes shape data. The shape data represents a shape of a wavefront in a area of the beam. Each element includes status data. The status data is a confidence indicator of ability of the shape data to represent the shape of the wavefront with a particular level of accuracy. Calculating control data based on the shape data in the wavefront data and local gain. The local gain includes local gain elements. Each local gain elements is adjusted based on status data. Using the control data to adjust a shape of an illumination wavefront of an illumination beam used to illuminate the fundus.

18 Claims, 12 Drawing Sheets

WAVEFRONT CORRECTION METHOD FOR ADAPTIVE OPTICS SYSTEM

CROSS-REFERENCE TO RELATED APPLICATION

This is a continuation, and claims the benefit, of U.S. patent application Ser. No. 15/099,435 filed Apr. 14, 2016 (now U.S. Pat. No. 9,808,153). U.S. patent application Ser. No. 15/099,435 is hereby incorporated by reference herein in its entirety.

BACKGROUND

Field of Art

The present disclosure relates to a system and method for controlling an adaptive optics system for an ophthalmic apparatus.

Description of the Related Art

Ophthalmoscopes, ophthalmic image pickup apparatuses, fundus imaging systems such as: scanning laser ophthalmoscopes (SLOs) that irradiate the fundus with a laser in two dimensions; and optical coherence tomographs (OCTs) that utilizes the interference of low coherence light have been developed and commercialized. Thus, SLOs and OCTs have become important tools for the study of the human fundus in both normal and diseased eyes.

The resolution of such ophthalmic image pickup apparatuses has recently been improved by, for example, achieving high numerical aperture (NA) of irradiation laser light. However, when an image of the fundus is to be acquired, the image must be acquired through optical tissues including the cornea and the crystalline lens. As the resolution increases, the aberrations of the cornea and the crystalline lens have come to significantly affect the quality of acquired images.

AO-SLO and AO-OCT in which the adaptive optics (AO) are a correction optical system that measures the aberration of the eye and corrects for the aberration have been pursued to improve the resolution of these systems. The AO-SLO and AO-OCT generally measure the wavefront of the eye using a Shack-Hartmann wavefront sensor system. A deformable mirror or a spatial-phase modulator is driven to correct the measured wavefront, and an image of the fundus is acquired, thus allowing AO-SLO and AO-OCT to acquire high-resolution images.

SUMMARY

An embodiment is a method for a controller to control an adaptive optics scanning laser ophthalmoscope. The method may comprise receiving from the ophthalmoscope a first set of wavefront data comprising a plurality of wavefront elements. Each particular wavefront element may be associated with a particular area of a received beam of light received from a fundus being imaged by the ophthalmoscope. Each particular wavefront element may include wavefront shape measurement data. The wavefront shape measurement data may be representative of a shape of a wavefront of the received beam of light in a particular area of the received beam of light. Each particular wavefront element may also include status measurement data. The status measurement data may be a confidence indicator of ability of the wavefront shape measurement data to represent the shape of the wavefront of the received beam of light in the particular area of the received beam of light with a particular level of accuracy. The method may also comprise calculating a second set of control data based on the wavefront shape measurement data in the wavefront data and a third set of local gain. The third set of local gain may include a plurality of local gain elements. Each element among the plurality of local gain elements may be adjusted based on one or more of the status measurement data. The method may also comprise transmitting the second set of control data to the ophthalmoscope. The ophthalmoscope uses the second set of control data to adjust a shape of an illumination wavefront of an illumination beam used to illuminate the fundus.

In some embodiments calculating the second set of control data may include using the following equation:

$$x = G_1 B(s G_2)$$

$$\begin{bmatrix} x_1 \\ x_2 \\ x_3 \\ \vdots \\ x_n \end{bmatrix} = G_1 \begin{bmatrix} B_{1,1} & B_{1,2} & B_{1,3} & \cdots & B_{1,m} \\ B_{2,1} & B_{2,2} & B_{2,3} & \cdots & B_{2,m} \\ B_{3,1} & B_{3,2} & B_{3,3} & \cdots & B_{3,m} \\ \cdots & \cdots & \cdots & \ddots & \cdots \\ B_{n,1} & B_{n,2} & B_{n,3} & \cdots & B_{n,m} \end{bmatrix} \left( \begin{bmatrix} s_1 \\ s_2 \\ s_3 \\ \vdots \\ s_m \end{bmatrix} \begin{bmatrix} G_{2_1} & 0 & 0 & \cdots & 0 \\ 0 & G_{2_2} & 0 & \cdots & 0 \\ 0 & 0 & G_{2_3} & \cdots & 0 \\ \vdots & \vdots & \vdots & \ddots & \vdots \\ 0 & 0 & 0 & \cdots & G_{2_m} \end{bmatrix} \right)$$

The matrix x may be representative of the second set of control data. The matrix B may be representative of a command matrix. The matrix s may be representative of the wavefront shape measurement data in the first set of wavefront data. Each wavefront shape element $s_i$ may be associated with the wavefront shape measurement data associated with element i and may be representative of the wavefront shape in a particular area i of the received beam of light. The matrix $G_2$ may be representative of the local gain based upon the status measurement data in the first set of wavefront data. Each local gain element $G_{2_i}$ may be calculated based upon status measurement data associated with the particular area i. The value $G_1$ may be representative of a global gain.

In some embodiments, calculating the second set of control data may include using the following equation:

$$x = G_1(Bs)G_3$$

$$\begin{bmatrix} x_1 \\ x_2 \\ x_3 \\ \vdots \\ x_n \end{bmatrix} = G_1 \begin{bmatrix} B_{1,1} & B_{1,2} & B_{1,3} & \cdots & B_{1,m} \\ B_{2,1} & B_{2,2} & B_{2,3} & \cdots & B_{2,m} \\ B_{3,1} & B_{3,2} & B_{3,3} & \cdots & B_{3,m} \\ \cdots & \cdots & \cdots & \ddots & \cdots \\ B_{n,1} & B_{n,2} & B_{n,3} & \cdots & B_{n,m} \end{bmatrix} \begin{bmatrix} s_1 \\ s_2 \\ s_3 \\ \vdots \\ s_m \end{bmatrix} \begin{bmatrix} G_{3_1} & 0 & 0 & \cdots & 0 \\ 0 & G_{3_2} & 0 & \cdots & 0 \\ 0 & 0 & G_{3_3} & \cdots & 0 \\ \vdots & \vdots & \vdots & \ddots & \vdots \\ 0 & 0 & 0 & \cdots & G_{3_n} \end{bmatrix}$$

The matrix x may be representative of the second set of control data. Each control data element k may be used to adjust the shape of the illumination wavefront in a particular illumination area k of the illumination beam. The matrix B may be representative of a command matrix. The matrix s may be representative of the wavefront shape measurement data in the first set of wavefront data. Each wavefront shape element $s_i$, may be associated with the wavefront shape information associated with element i and may be representative of a wavefront shape in the particular wavefront detection area. Each illumination area k may be in an optically conjugate position with a particular set of one or more wavefront detection areas. The matrix $G_3$ may be representative of the local gain based upon the status measurement data in the wavefront data. Each local gain element $G_{3_k}$ may be calculated based on one or more status measurement data associated with the particular set of one or more wavefront detection areas that are in the optically conjugate position with the illumination area k; and the value $G_1$ may be representative of global gain.

In some embodiments the first set of wavefront data may include m wavefront elements. The local gain may include a set of m local gain values. Each local gain value i may be applied to a corresponding wavefront shape information element i during the calculation of the second set of control data.

In some embodiments, the second set of control data may include n control elements. The local gain may include a set of n local gain values. Each local gain value k may be used to calculate a corresponding control element k.

In some embodiments, the status measurement data for each particular wavefront element may be representative of a signal intensity associated with data used to calculate the wavefront shape measurement data in the particular area of the received beam of light associated with the particular wavefront element.

In some embodiments, the status measurement data for each particular wavefront element may be an estimate of a diameter of a spot associated with information used to calculate the shape of the wavefront in the particular area of the received beam of light associated with particular wavefront element.

In some embodiments the adaptive optics scanning laser ophthalmoscope being controlled may include a Shack-Hartmann sensor that may be used to produce the first set of wavefront data. Each particular wavefront element in the first set of wavefront data may be associated with a particular lenslet in the Shack-Hartmann sensor. The status measurement data for each particular wavefront element may be an estimate of a diameter of a spot associated with information used to calculate the wavefront shape measurement data.

In some embodiments, a non-transitory computer readable medium encoded with instructions for a controller to control an adaptive optics scanning laser ophthalmoscope.

In some embodiments, a controller for controlling an adaptive optics scanning laser ophthalmoscope, the controller comprising: a memory; and a processor. The processor may receive from the ophthalmoscope a first set of wavefront data comprising a plurality of wavefront elements. The processor may store first set of wavefront data in the memory. Each particular wavefront element may be associated with a particular area of a received beam of light received from a fundus being imaged by the ophthalmoscope. Each particular wavefront element may include wavefront shape measurement data. The wavefront shape measurement data may be representative of a shape of a wavefront of the received beam of light in a particular area of the received beam of light. Each particular wavefront element may include status measurement data. The status measurement data may be a confidence indicator of ability of the wavefront shape measurement data to represent the shape of the wavefront of the received beam of light in the particular area of the received beam of light with a particular level of accuracy. The processor may calculate a second set of control data based on the wavefront shape measurement data in the wavefront data and a third set of local gain. The third set of local gain may include a plurality of local gain elements. Each element among the plurality of local gain elements may be adjusted based on one or more of the status measurement data. The processor transmits the second set of control data to the ophthalmoscope. The ophthalmoscope uses the second set of control data to adjust a shape of an illumination wavefront of an illumination beam used to illuminate the fundus.

In some embodiments, the controller further comprises the adaptive optics scanning laser ophthalmoscope controlled by the controller. In some embodiments, the controller further comprises a wavefront sensor. In some embodiments, the wavefront sensor may be a Shack-Hartmann sensor. In some embodiments, the controller further comprises a wavefront adjustment device. In some embodiments, the wavefront adjustment device may be a deformable mirror. In some embodiments, the wavefront adjustment device may include at least one liquid crystal element. In some embodiments, the wavefront adjustment device may include at least one spatial phase modulator.

BRIEF DESCRIPTION OF THE DRAWINGS

The accompanying drawings, which are incorporated in and constitute a part of the specification, illustrate exemplary embodiments.

DESCRIPTION OF THE EMBODIMENTS

Figure 1:
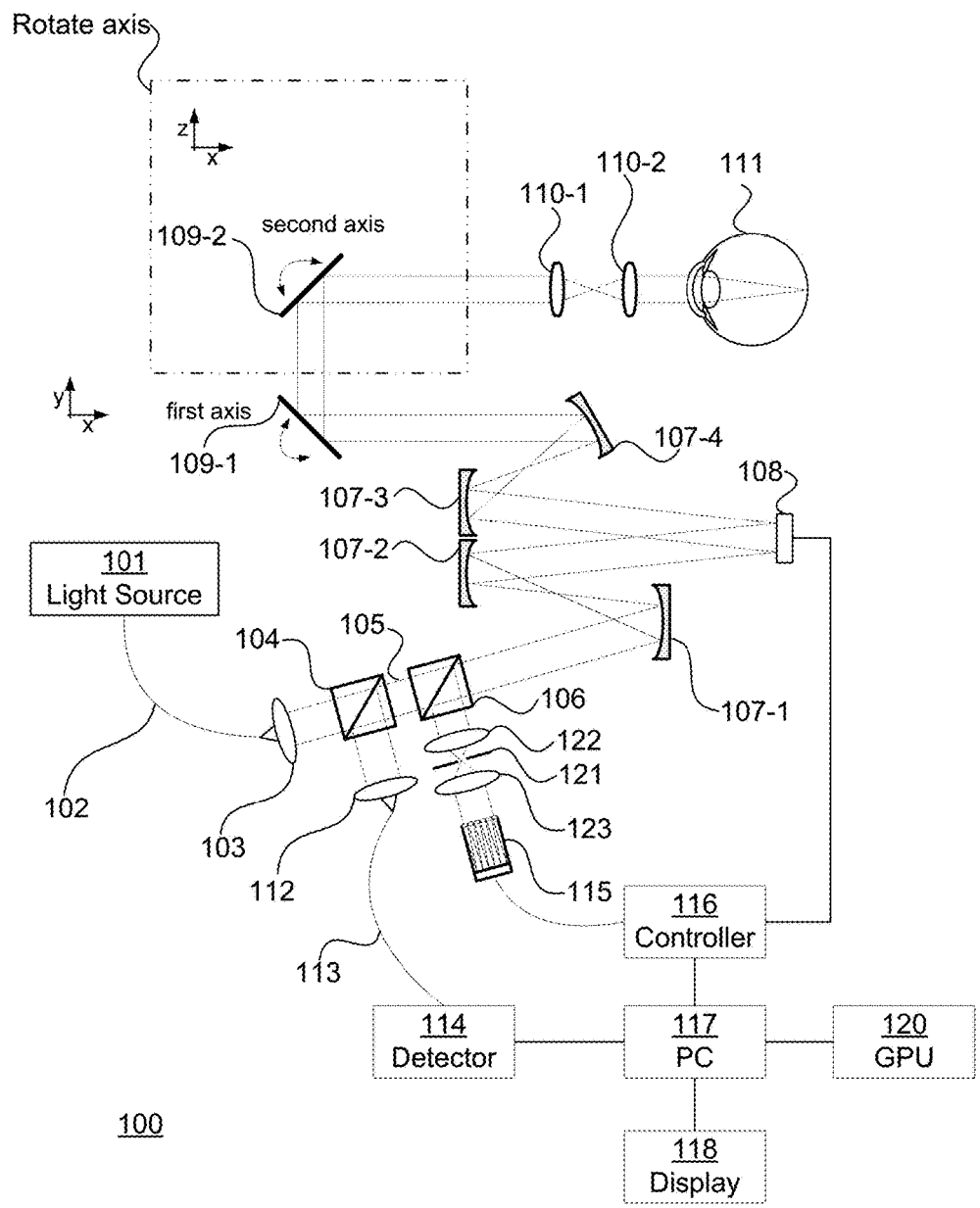
FIG. 1 is a generalized illustration of an apparatus in which an embodiment may be implemented.

Embodiments will be described below with reference to the attached drawings. Like numbers refer to like elements throughout. Exemplary embodiments will be described in detail with reference to the drawings below. It shall be noted that the following description is merely illustrative and exemplary in nature, and is in no way intended to limit the disclosure and its applications or uses. The relative arrangement of components and steps, numerical expressions and numerical values set forth in the embodiments do not limit the scope of the disclosure unless it is otherwise specifically stated. Techniques, methods, and devices which are well known by individuals skilled in the art may not have been discussed in detail since an individual skilled in the art would not need to know these details to enable the embodiments discussed below. Further, an image photographing apparatus as disclosed in the following which is used to inspect an eye as described below may also be used to inspect other objects including but not limited to skin, and internal organs.

Ophthalmoscope

A first embodiment is described with reference to a fundus image photographing apparatus (ophthalmoscope) such as the photographing apparatus illustrated in FIG. 1.

Embodiments are directed towards systems, methods, non-transitory computer readable medium, and software which are used in connection with an imaging system such as an ophthalmoscope 100. FIG. 1 is an illustration of an exemplary ophthalmoscope 100. An ophthalmoscope 100 is a system or apparatus for obtaining information about an interior portion of the eye 111 (e.g., the fundus).

An exemplary embodiment may be a scanning ophthalmoscope. A scanning ophthalmoscope scans a spot across the eye 111. The spot may be a spot of light from a light source 101 that is scanned across the eye 111.

In an exemplary embodiment 100, the spot of light is produced by a light source 101. The light source 101 may be incorporated into the ophthalmoscope 100; alternatively, the ophthalmoscope 100 may include an input for receiving the light source 101. The input for the light source 101 may be a fiber optic input 102 or a free space input (not shown). The light source 101 may be a laser, a broadband light source, or multiple light sources. In an exemplary embodiment, the light source 101 is a super luminescent diode (SLD) light source having a wavelength of 840 nm. The wavelength of the light source 101 is not particularly limited, but the wavelength of the light source 101 for fundus image photographing is suitably set in a range of approximately 800 nm to 1,500 nm in order to reduce glare perceived by a person being inspected and to maintain imaging resolution.

In an exemplary embodiment, light emitted from the light source 101 passes through a single-mode optical fiber 102, and is radiated as collimated light (measuring light 105) by a collimator 103.

In an exemplary embodiment, the polarization of the irradiated light may be adjusted by a polarization adjusting member 119 (not shown) provided in a path of the single-mode optical fiber 102. In an alternative configuration, the light source 101 is polarized and single-mode optical fiber 102 is polarization maintaining fiber. In another configuration, the polarization adjusting member may be placed after the collimator 103. Alternatively, the polarization adjusting member may be replaced with a polarizer. In an alternative embodiment, the irradiated light may be unpolarized, depolarized, or the polarization may be uncontrolled.

The measuring light 105 radiated from the collimator 103 passes through a light division portion 104 including a beam splitter. An exemplary embodiment includes an adaptive optical system.

The adaptive optical system may include a light division portion 106, a wavefront sensor 115, wavefront adjustment device 108, a pinhole 119, a lens 122, a lens 123, and reflective mirrors 107-1 to 107-4 for guiding the measuring light 105 to and from those components. The reflective mirrors 107-1 to 107-4 are provided to guide the measuring light 105 to and from the pupil of an eye 111, the wavefront sensor 115, and the wavefront adjustment device 108. The reflective mirrors may be replaced with suitable optics, such as lenses and/or apertures. Likewise, the lenses may be replaced with mirrors. The wavefront sensor 115 and the wavefront adjustment device 108 may be in an optically conjugate relationship. A beam splitter may be used as the light division portion 106. The wavefront sensor 115 may be a Shack-Hartmann sensor or other type of sensor that gathers information that is representative on the spatial nature of the wavefront of light coming from the subject. Other examples of types of sensors that provide information about the shape of a wavefront include but are not limited to: a pyramid wavefront sensor; common path interferometer; Foucault knife-edge tester; a multilateral shearing interferometer; Ronchi tester; and Shearing Interferometer.

A pinhole 121 and lenses 122 and 123 may be placed between the wavefront sensor 115 and the beam splitter 106. The pinhole 121, lens 122, and lens 123 are arranged to ensure that light from the surface of the retina is detected by the wavefront sensor 115 while other light is blocked. Lenses 122-123 may be replaced with mirrors.

The measuring light 105 passing through the light division portion 106 is reflected by the reflective mirrors 107-1 and 107-2 so as to enter the wavefront adjustment device 108. The measuring light 105 is reflected by the wavefront adjustment device 108 and is further reflected by the reflective mirrors 107-3 and 107-4.

The wavefront adjustment device 108 maybe a transmissive device or a reflective device. The wavefront adjustment device 108, may be an addressable spatial light phase modulator that allows relative phases across a beam coming into the wavefront adjustment device 108 to be adjusted such that relative phases across the beam coming out of the wavefront adjustment device 108 are adjustable. In an exemplary embodiment, one or two spatial phase modulators each including a liquid crystal element is used as the wavefront adjustment device 108. The liquid crystal element may modulate a phase of only a specific polarized component. In which case, two liquid crystal elements may be employed to modulate substantially orthogonal polarized components of the measuring light 105. In an alternative embodiment, the wavefront adjustment device 108 is a deformable mirror.

The measuring light 105 reflected off mirror 107-4 is two-dimensionally scanned by a scanning optical system 109. In an exemplary embodiment, the scanning optical system 109 includes a first scanner 109-1 and a second scanner 109-2. The first scanner 109-1 rotates around the first axis, while the second scanner 109-2 rotates around a second axis. The first axis is substantially orthogonal to the second axis. Substantially in the context of the present disclosure means within the alignment and measurement tolerances of the system. The scanning optical system 109 may include one or more additional scanners 109-3 (not shown) which are used for steering the scanning area to different parts of the fundus.

FIG. 1 illustrates the first scanner 109-1 rotating in the x-y plane, while the second scanner 109-2 is rotating in the z-x plane. In the context of the present disclosure, rotating the measuring light 105 in a first plane around the first axis is equivalent to rotating the measuring light 105 in the first plane and is equivalent to scanning the spot of light in the main scanning direction or the lateral direction of the object being imaged. In the context of the present disclosure, rotating the measuring light 105 in a second plane around the second axis is equivalent to scanning the spot of light in the sub-scanning direction or the longitudinal direction of the object being imaged. The sub-scanning direction is substantially orthogonal to the main scanning direction.

A scanning period of the first scanner 109-1 is less than the scanning period of the second scanner 109-2. The order of the first scanner 109-1 and the second scanner 109-2 may be exchanged without impacting the operation of an exemplary embodiment. The first scanner 109-1 may operate in a resonant scanning mode.

In an exemplary embodiment, the scanning optical system 109 may be a single tip-tilt mirror that is rotated around the first axis and around the second axis that is substantially orthogonal to the first axis. An exemplary embodiment may also use non-mechanical beam steering techniques.

In an exemplary embodiment, the first scanner 109-1 and the second scanner 109-2 are galvano-scanners. In another exemplary embodiment, one of the first scanner 109-1 and the second scanner 109-2 is a resonant scanner. The resonant scanner may be used for the main scanning direction. The resonant scanner may be tuned to oscillate at a specific frequency. There may be additional optical components, such as lenses, mirrors, apertures, and etc. between the scanners 109-1, 109-2, and other optical components. These additional optical components may be arranged such that the light is focused onto the scanners, in a manner that is optically conjugate with all of or one or more of the subject 111, the wavefront adjustment device 108, the wavefront sensor 115, and a detector 114.

The measuring light 105 scanned by the scanning optical system 109 is radiated onto the eye 111 through eyepieces 110-1 and 110-2. The measuring light radiated to the eye 111 is reflected, scattered, or absorbed by the fundus 111. When the eyepieces 110-1 and 110-2 are adjusted in position, suitable irradiation may be performed in accordance with the diopter of the eye 111. Lenses may be used for the eyepiece portion in this embodiment, but other optical components such as spherical mirrors may also be used.

Light which is produced by reflection, fluorescence, and/or scattering by a fundus of the eye 111 then travels in the reverse direction along the same path as the incident light. A part of the reflected light is reflected by the light division portion 106 to the wavefront sensor 115 to be used for measuring a light beam wavefront.

In an exemplary embodiment, a Shack-Hartmann sensor is used as the wavefront sensor 115. However, an exemplary embodiment is not limited to a Shack-Hartmann sensor. Another wavefront measurement unit, for example, a curvature sensor may be employed or a method of obtaining the wavefront by reverse calculation from the spot images may also be employed.

In FIG. 1, when the reflected light passes through the light division portion 106, a part thereof is reflected on the light division portion 104 and is guided to a light intensity sensor 114 through a collimator 112 and an optical fiber 113. The light intensity sensor 114 converts the light into an electrical signal. The electrical signal is processed by a PC 117 or other suitable processing device into an image of the subject and the image is displayed on a display 118.

The wavefront sensor 115 is connected to an adaptive optics controller 116. The received wavefront is transferred to the adaptive optics control unit 116. The wavefront adjustment device 108 is also connected to the adaptive optics control unit 116 and performs modulation as instructed by the adaptive optics control unit 116. The adaptive optics controller 116 calculates a modulation amount (correction amount) to obtain a wavefront having less aberration based on the wavefront obtained by a measuring result of the wavefront sensor 115, and instructs the wavefront adjustment device 108 to perform the modulation according to the modulation amount. The wavefront measurement and the instruction to the wavefront adjustment device are repeated and a feedback control is performed so as to obtain a suitable wavefront.

In an exemplary embodiment the light division portions 104 and 106 are partially reflective mirrors. In an alternative exemplary embodiment, the light division portions 104 and/or 106 may include fused fiber couplers. In another alternative exemplary embodiment, the light division portions 104 and/or 106 may include dichroic reflectors, in which case a different wavelength of light is used for obtaining an image of the fundus then is used for detecting the spatial phase image that controls the adaptive optics system.

The detector 114 may detect reflections or fluorescence associated with the scanning spot. The detection system may make use confocal microscopy techniques in which an aperture associated with the scanning spot is used to increase the resolution and/or contrast of the detection system.

The adaptive optics system described above includes at least the wavefront sensor 115 and the wavefront adjustment device 108 so that the aberration of the subject's eyes can be measured and compensated for. A deformable mirror (DM) or a spatial light phase modulator (SLM) can be used as the wavefront adjustment device 108. Since the typical SLM has a large number of actuators, it can modulate wavefront more precisely than DM can. A liquid crystal on silicon spatial light modulator (LCOS-SLM) may be used as the wavefront adjustment device 108. The LCOS-SLM 108 can be controlled to provide a precise spatial modulation of the phase of the beam that is used to illuminate the subject.

Controller

Figure 2:
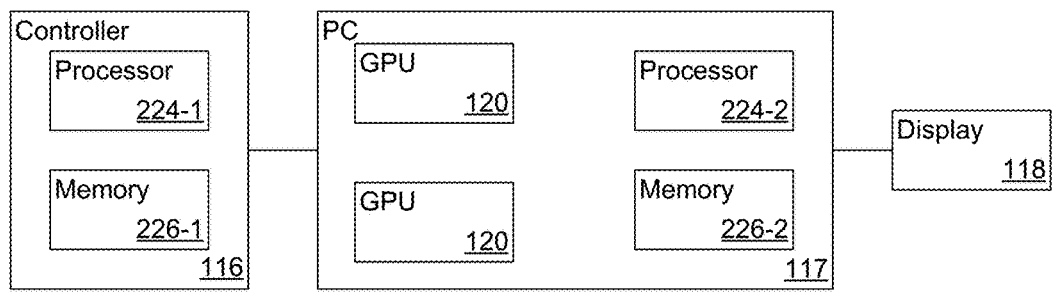
FIG. 2 is an illustration of a controller that may be used in an embodiment.

FIG. 2 is an illustration of the PC 117 and controller 116 that may be used in an embodiment. The controller 116 receives input values and outputs control values. The controller 116 may be a general purpose computer, a device specifically designed to controller the ophthalmoscope or measuring instrument, or a hybrid device that uses some custom electronics along with a general purpose computer 117. The input values and control values maybe digital values or analog values. The controller 116 may include an analog to digital converter (ADC) and a digital to analog converter (DAC). The input values may include one more values such as a signal from the wavefront sensor 115, a signal from the detector 114, and one or more values from one or more other sensors. The control values may include control values sent to a wavefront adjustment device 108 and values to one or more of the scanners 109-1, 109-2. The control values may include additional values to other components of the instrument.

The controller 116 includes a processor 224-1. The processor 224-1 may be a microprocessor, a CPU, an ASIC, a DSP, and/or a FPGA. The processor 224-1 may refer to one or more processors that act together to obtain a desired result. The controller 116 may include a memory 226-1. The memory 226-1 may store calibration information. The memory 226-1 may also store software for controlling the ophthalmoscope. The memory 226-1 may take the form of a non-transitory computer readable storage medium. The non-transitory computer readable storage medium may include, for example, one or more of a hard disk, a random-access memory (RAM), a read only memory (ROM), a distributed storage system, an optical disk (CD, DVD or Blu-Ray Disc, a flash memory device, a memory card, or the like. The controller 116 may include input devices such as a keyboard, a mouse, a touch screen, knobs, switches, and/or buttons.

The controller 116 may be connected to a computer (PC) 117 via a direct connection, a bus, or via a network. The computer 117 may include input devices such as a keyboard, a mouse, and/or a touch screen. The computer 117 may be connected to a display 118. The results and/or data produced by the ophthalmoscope 100 may be presented to a user via the display 118. The PC may include a processor 224-2, a memory 226-2. The PC may also include one or more GPUs 120

Adaptive Optics

Adaptive optics systems are typically controlled using a feedback loop type system. In these AO feedback loops aberrations are measured and then the aberrations are corrected are processed one after another continuously.

Figure 3A:
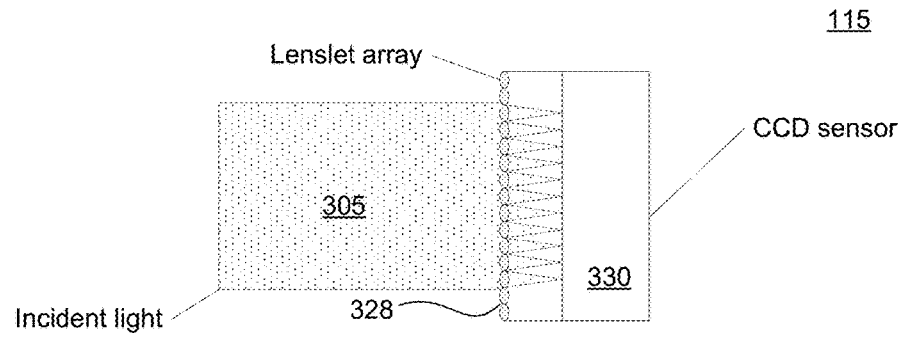
FIGS. 3A-D are generalized illustrations of a wavefront sensor and Hartmann spots as might be used in an embodiment.
Figure 3B:
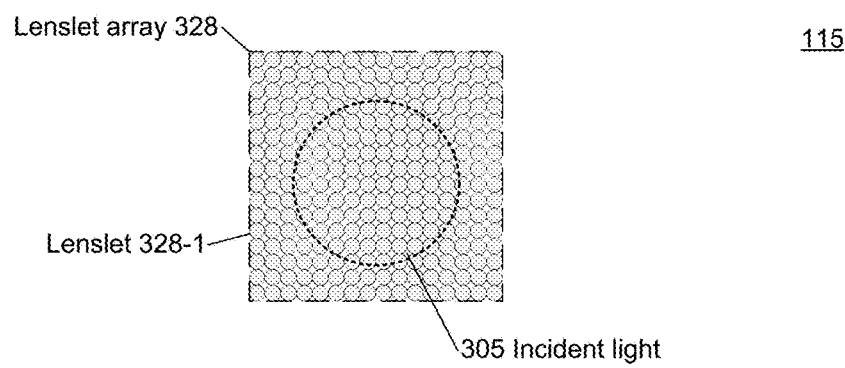

FIGS. 3A-B are illustrations of a Shack-Hartmann type wavefront sensor 115 which may be used in an embodiment. FIG. 3A is a side view of the Shack-Hartmann type wavefront sensor 115. FIG. 3B is a top view of the Shack-Hartmann type wavefront sensor 115. The Shack-Hartmann type wavefront sensor 115 may include a CCD sensor 330 and a lenslet array 328 just in front of the CCD sensor 330. The lenslet array 328 is an array of lenslets 328-1. The light 305 from the subject 11 goes through the lenslet array 328 to divide the light into multiple portions of the light. The divided light is then focused onto the surface of the CCD sensor 330 by the lenslet-array 328.

Figure 3C:
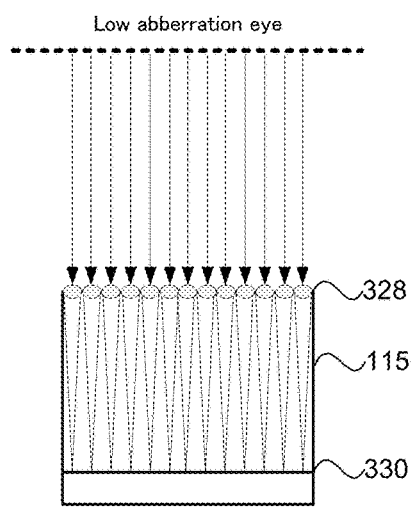
Figure 3C:
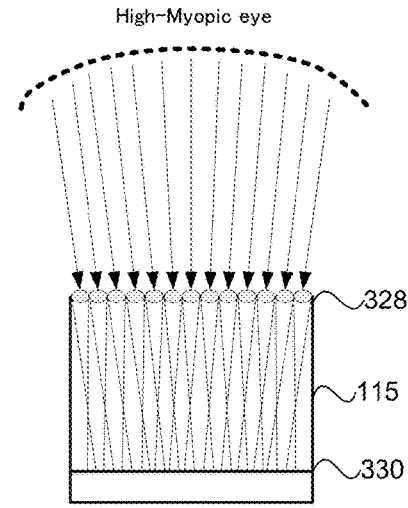
Figure 3C:
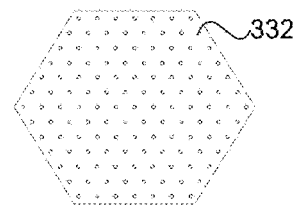
Figure 3D:
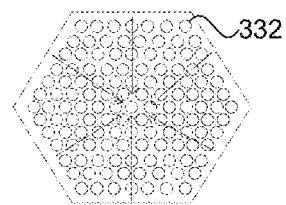

Low aberrated light from a low aberration eye can shape small spots 324 on the CCD sensor surface 330 of the wavefront sensor 115 as illustrated in FIG. 3C. When the spots 332 are small, it is easy to detect a center (or centroid) of the intensity of the spots and to calculate the shape of the wavefront. If the light is aberrated, the spots 332 get blurred, and it can be difficult to detect the center (or centroid) of the intensity as illustrated in FIG. 3D.

Figure 4A:
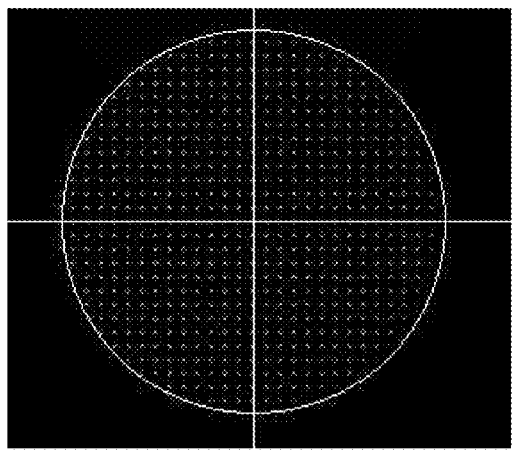
FIGS. 4A-D are examples of wavefront spots as detected by a wavefront sensor.
Figure 4B:
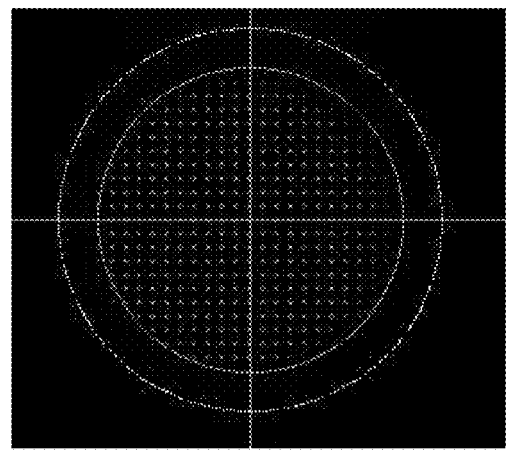
Figure 4C:
Figure 4D:

FIG. 4A is an illustration of a Hartmann image from a normal eye and a target illustrating an estimated location of the pupil based on the Hartmann image. FIG. 4B is an illustration of a Hartmann image from a myopic eye and a target illustration an estimated location of the pupil based on the Hartmann image, and a target illustrating a relative location of the illumination beam based upon the system alignment. FIG. 4C is a zoomed in image of 9 spots from the Hartmann image of a normal eye. FIG. 4D is a zoomed in image of 9 spots from the Hartmann image of a myopic eye.

The wavefront sensor 115 produces measured aberration information which is used in an AO feedback control loop as used in an embodiment. The measured aberration information may take the form of displacement data. That displacement data may be converted to one or more Zernike coefficients. These Zernike coefficients may then be converted into command values for the wavefront adjustment device 108.

The displacement information s may also be directly used to generate command values x for the wavefront adjustment device 108. Generating the command values x may include the use of an Influence Function A which represents a displacement matrix related to each actuator movement (or pixel) of the wavefront adjustment device 108 as described by equation (1). In which s is the displacement information based upon the measured wavefront sensor signal. In which A is the Influence function. In which x is the command values sent to the wavefront adjustment device 108.

$$s = Ax \quad (1)$$

Generating the command values may also include the use of a Command Matrix B which is the pseudo inverse of the Influence Function A as described equation (2). In which, the matrix B is the command matrix.

$$B = A^+ \quad (2)$$

The command values x may be generated by multiplying the measured displacement information s by the Command Matrix B. In order to stabilize the AO control loop and prevent under or over correction an appropriate gain parameter G may be applied to the command values the wavefront adjustment device 108 as describe in equation (3). In which, G is the gain parameter. Equation (3) represents an AO control loop which uses an open loop control system. AO feedback control may also use closed loop control, in which case the calculated command value is combined with the previous command value. In this case, the gain parameter G may be 1 the first time the command values x are calculated. Equation (3) can be modified to describe a close loop control system using equation (3').

$$x = GBs \quad (3)$$

$$x_n = GBs_n + x_{n-1} \quad (3')$$

Figure 5A:
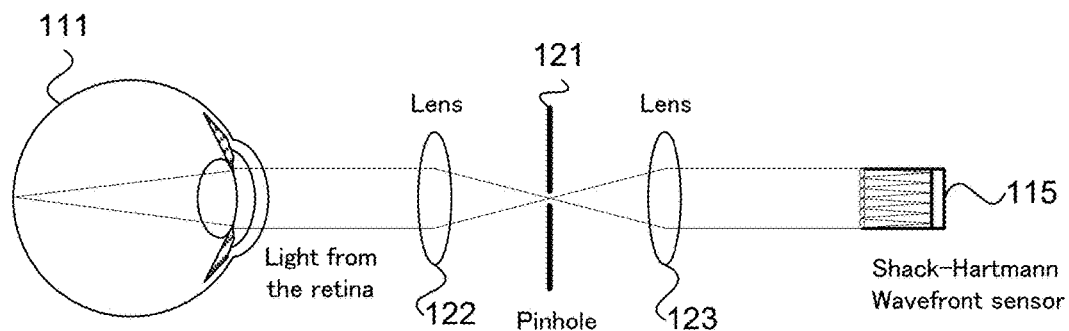
FIGS. 5A-B are illustrations of how a pinhole may be used in combination with a wavefront sensor.
Figure 5B:
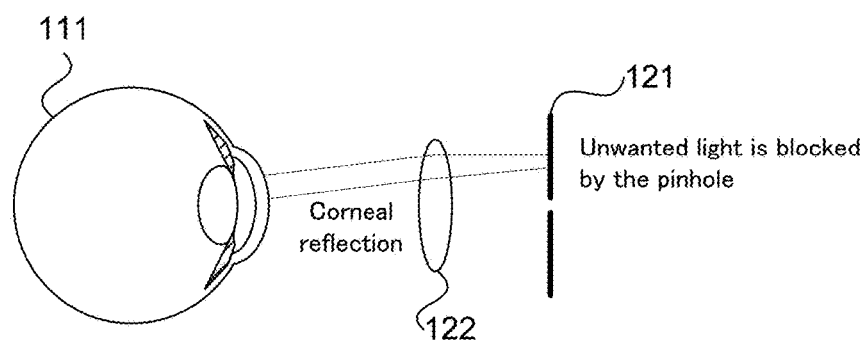

To improve the accuracy of the wavefront measurement, the pinhole 121 may be placed in front of the wavefront sensor 115 to block light coming from surfaces other than the retina especially from the cornea as illustrated in FIG. 5B. This pinhole can also block the back reflection light from other optical elements in the optical system. FIGS. 5A-B are generalized illustrations of such a system. FIG. 5A illustrates the subject 111 such as an eye being imaged by a system that includes a wavefront sensor 115. The pinhole 121 is placed between the subject 111 and the wavefront sensor 115. The pinhole 121 also placed between 2 lenses 122 and 123. The pinhole 121 is positioned between 2 lenses 122 and 123 such that extraneous light does not reach the wavefront sensor 115. The size of the pinhole is such that it blocks light from the cornea as illustrated in FIG. 1B. The pinhole 121 allows light to pass mainly from the retina of the subject 111 as illustrated in FIG. 1A. The wavefront measurement is very important part of this feedback loop because if the wavefront is measured incorrectly, the wavefront corrector does not compensate for the real aberration and may generate an additional aberration. Sometimes the wavefront measurement is disturbed by various factors. Direct reflection light from the surface of the cornea, cataract, pupil shrinking, eye lash and eye lid are main reasons for disturbing the aberration measurement. Reflection light from the cornea can be blocked by a pinhole 121 in front of the Shack-Hartman sensor as illustrated in FIG. 5B.

Figure 6A:
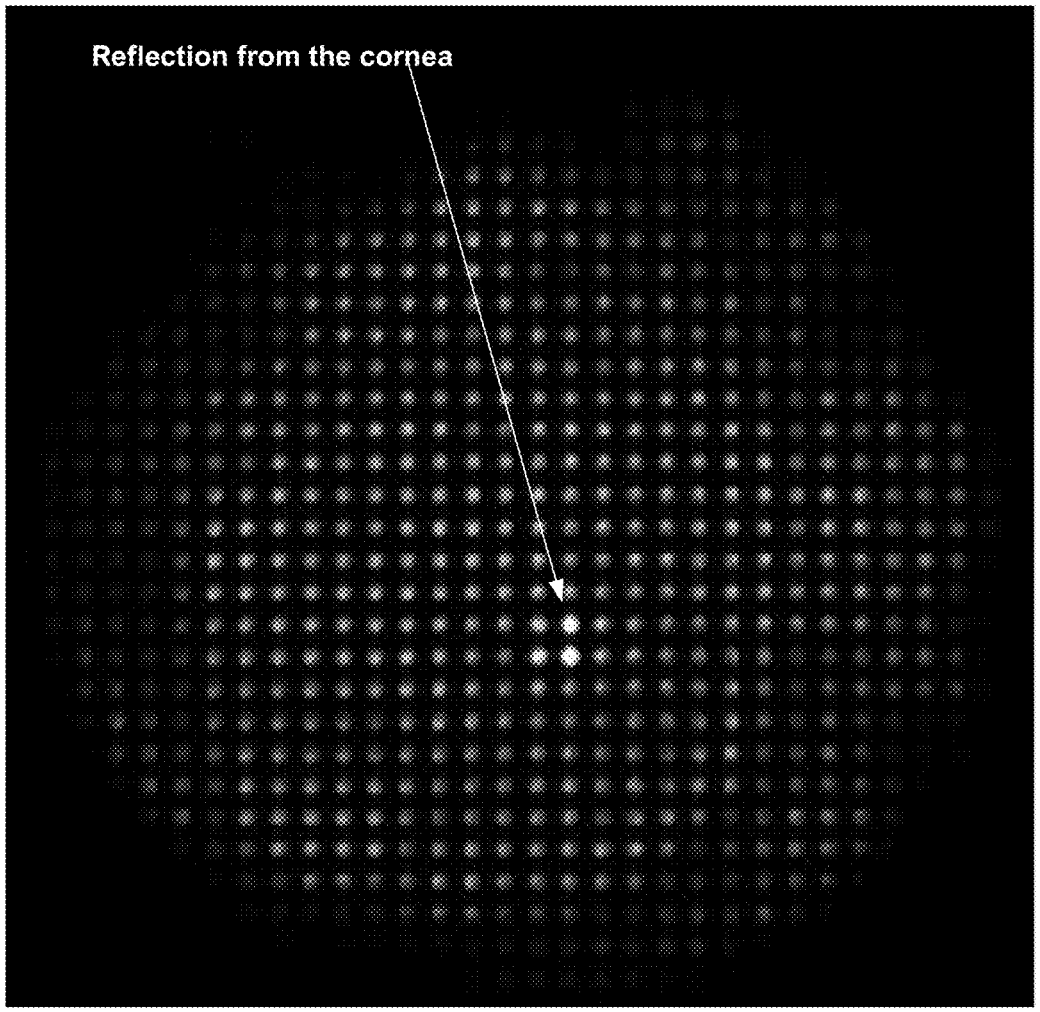
FIGS. 6A-E are examples of wavefront spots as detected by a wavefront sensor.
Figure 6B:
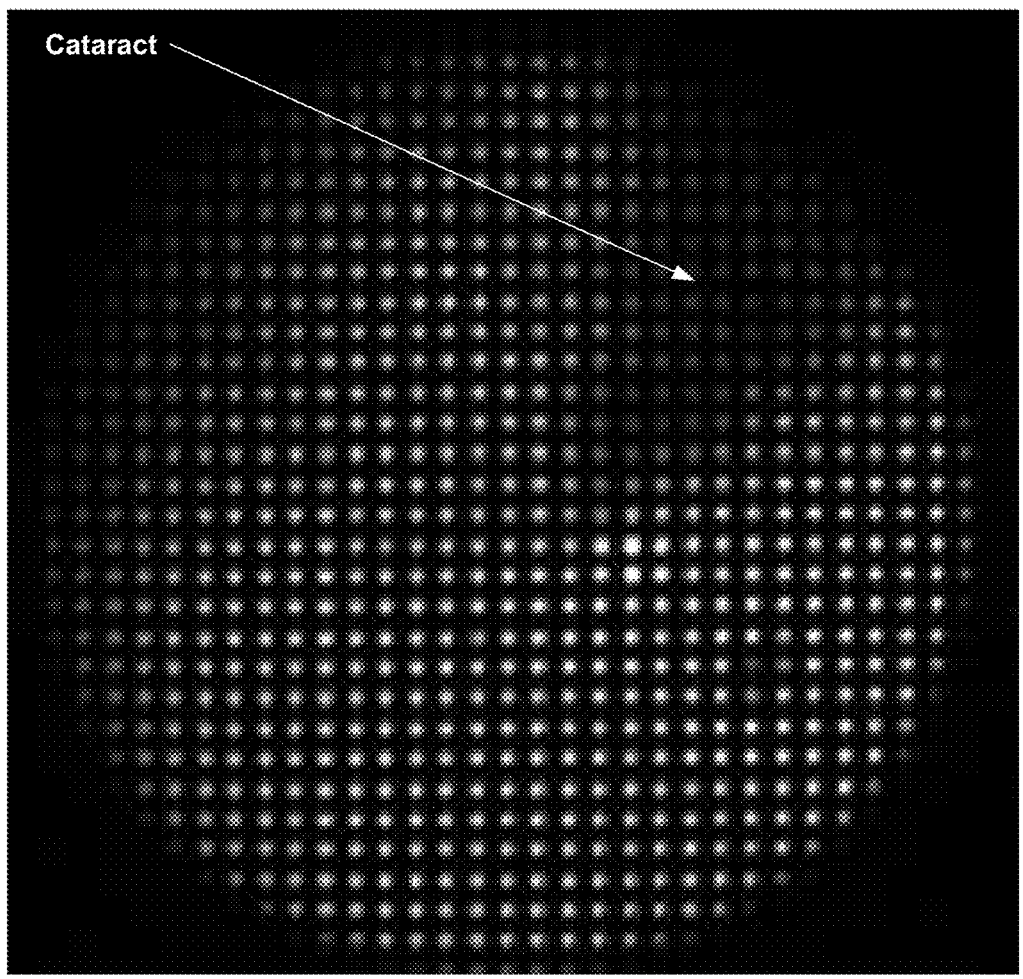
Figure 6C:
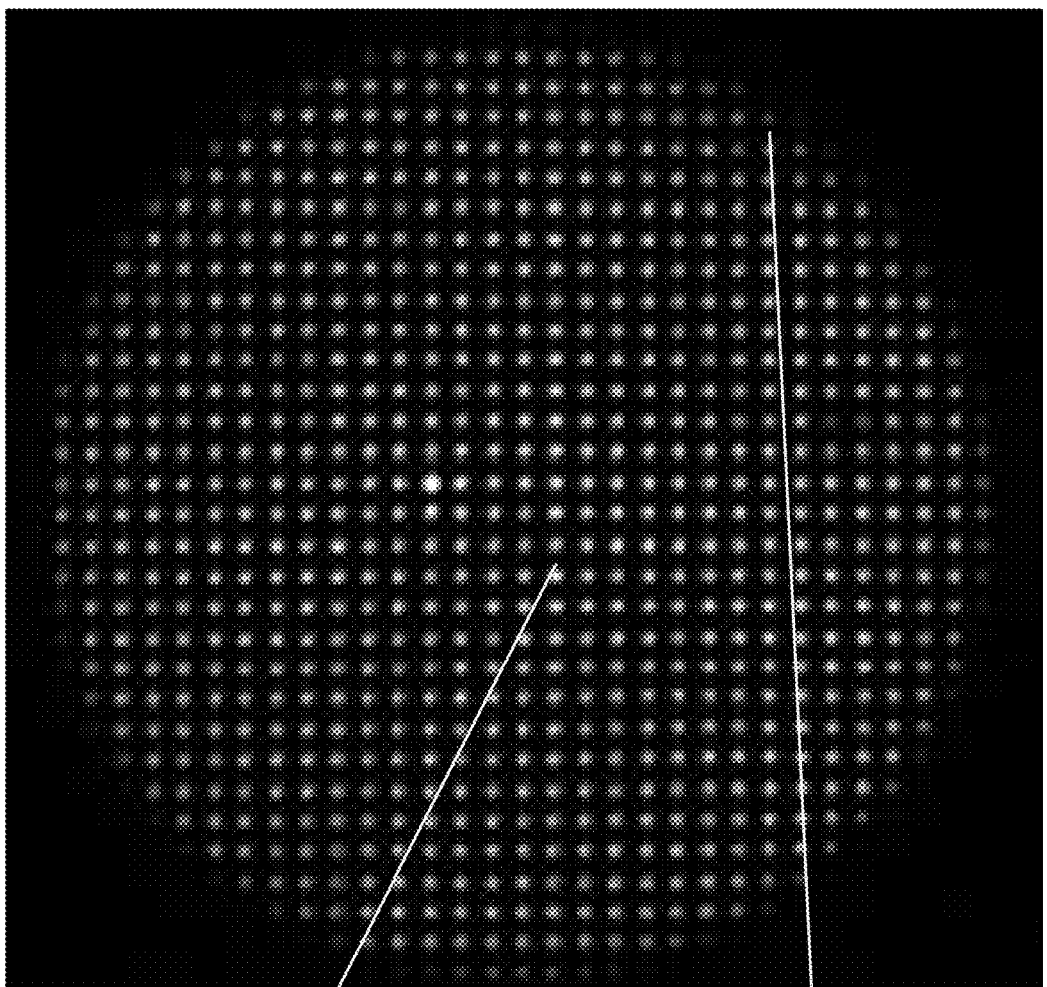
Figure 6D:
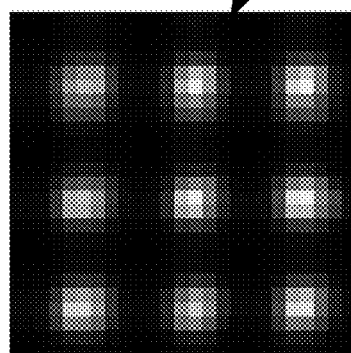
Figure 6E:
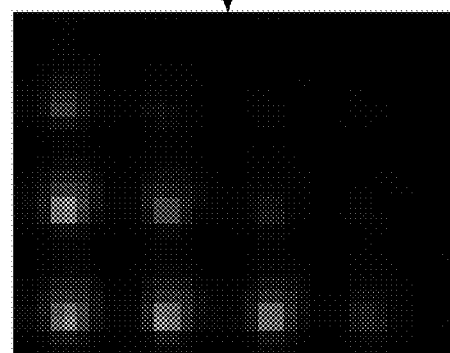

The pinhole 121 is not a perfect solution to this problem, and strong disturbing signal can be detected in some case. For example, FIG. 6A is an illustration of a Hartmann image in which the reflection from the cornea can be seen. Cataracts can also decreases spots signal in the Hartmann image as illustrated in FIG. 6B. Even under normal measurement conditions, spot signals at the edge may be weaker than spot signals at the center as illustrated in FIG. 6C. FIG. 6D is a zoomed in image of some Hartmann spots at the center of the Hartmann image. FIG. 6E is a zoomed in image of some Hartmann spots at the edge of the Hartmann image.

Figure 6F:
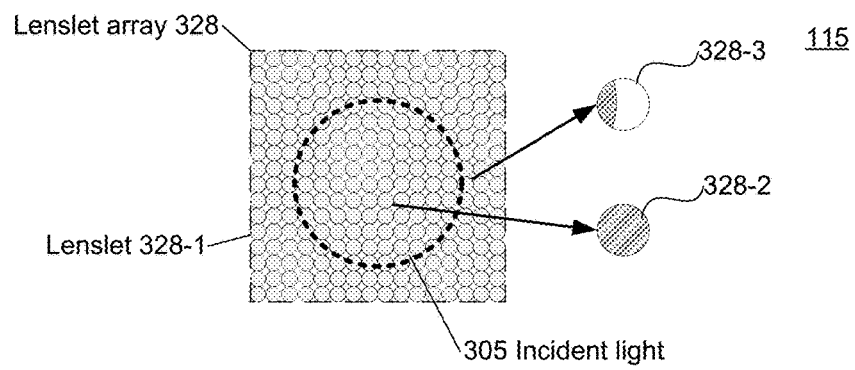
FIGS. 6F-G are illustrations of a lenslet array of a wavefront sensor is illuminated.
Figure 6G:
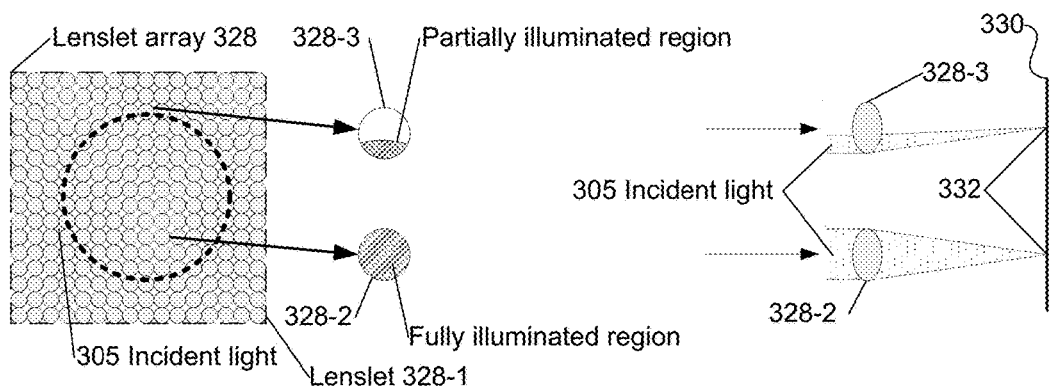

One reason for this lower intensity at the edge as illustrated in FIG. 6E is because only a limited area of a lenslet 328-1 may be illuminated by the incident light near the edge of wavefront sensor 115. On the other hand, the whole area of lenslet 328-1 is illuminated at the center of the wavefront sensor 115. FIG. 6F is an illustration of the normal illumination of the lenslet array 328 with incident light 305. In FIG. 6F a center lenslet 328-2 is fully illuminated and an edge lenslet 328-3 is partially illuminated. FIG. 6G is another illustration of the normal illumination of the lenslet array 328 with the incident light. In FIG. 6G another center lenslet 328-2 is fully illuminated and another edge lenslet 328-3 is partially illuminated. FIG. 6G also shows the side profile of the edge illumination and how a partially illuminated lenslet 328-3 would be measured by the CCD sensor 330 when compared to the same illumination of a fully illuminated lenslet 328-2.

As the intensity of the spot signal is decrease, then the influence of noise increases. To calculate the displacement, center of intensity is calculated first. But if the illumination is not uniform, calculation of the center of intensity is not accurate. As a result, spot displacement at weaker illuminated area is not as accurate as one of a fully illuminated area. It makes wavefront measurement incorrect and makes AO control less precise and unstable.

In an embodiment the local gain of the AO control is adjusted according to the Shack-Hartman sensor spots' condition. An embodiment may make use of 2 gain parameters: $G_1$ and $G_2$. $G_1$ is a scaler value for entire AO control loop. $G_2$ is an array of values $G_2=[g_1 \ldots g_m]$ wherein m is number of lenslets 328-1 in the lenslet array 328. The array $G_2$ is a matrix which consists of local gain values for each spot in the Shack-Hartman sensor 115. Equation (4) described $G_1$ may be applied to equation (3).

$$x = G_1 B s \quad (4)$$

The values x, B, and s are matrices in most cases, and can be described using equation (5).

$$\begin{bmatrix} x_1 \\ x_2 \\ x_3 \\ \vdots \\ x_n \end{bmatrix} = G_1 \begin{bmatrix} B_{1,1} & B_{1,2} & B_{1,3} & \cdots & B_{1,m} \\ B_{2,1} & B_{2,2} & B_{2,3} & \cdots & B_{2,m} \\ B_{3,1} & B_{3,2} & B_{3,3} & \cdots & B_{3,m} \\ \cdots & \cdots & \cdots & \ddots & \cdots \\ B_{n,1} & B_{n,2} & B_{n,3} & \cdots & B_{n,m} \end{bmatrix} \begin{bmatrix} s_1 \\ s_2 \\ s_3 \\ \vdots \\ s_m \end{bmatrix} \quad (5)$$

In which n is the number of actuators or pixels in the wavefront adjustment device 108, and the matrix x includes a set of control values $x_1$. In which m is the number of lenslets or their equivalents associated with the wavefront sensor 115, and the matrix s includes a set of measured wavefront sensor signal value $s_j$. The measured wavefront sensor signal value $s_j$ is the displacement associated with each spot j, lenslet j or their equivalent. The measured wavefront sensor signal value $s_j$ may be a displacement value or a slope that includes 2 values $s_j=[s_{j_x}, s_{j_y}]$. The command matrix B may be a n×m matrix as shown in equation (5). The command matrix includes commands $B_{i,j}$, which are calculated in the manner described above.

In an embodiment the gain of the AO control is adjusted according to the wavefront sensor's local condition as described by equation (6).

$$x = G_1 B(sG_2) \quad (6)$$

Equation (6) is substantially similar to equations (4)-(5) and includes the additional use of a matrix $G_2$ which may be used to represent the local gain associated with each spot. The matrix $G_2$ may be a diagonal matrix with m local gain elements $G_{2_j}$ associated with each spot j as illustrated in following rewritten version of equation (6) in which the matrix elements are specifically identified.

$$\begin{bmatrix} x_1 \\ x_2 \\ x_3 \\ \vdots \\ x_n \end{bmatrix} = \quad (6)$$

$$G_1 \begin{bmatrix} B_{1,1} & B_{1,2} & B_{1,3} & \cdots & B_{1,m} \\ B_{2,1} & B_{2,2} & B_{2,3} & \cdots & B_{2,m} \\ B_{3,1} & B_{3,2} & B_{3,3} & \cdots & B_{3,m} \\ \cdots & \cdots & \cdots & \ddots & \cdots \\ B_{n,1} & B_{n,2} & B_{n,3} & \cdots & B_{n,m} \end{bmatrix} \left( \begin{bmatrix} s_1 \\ s_2 \\ s_3 \\ \vdots \\ s_m \end{bmatrix} \begin{bmatrix} G_{2_1} & 0 & 0 & \cdots & 0 \\ 0 & G_{2_2} & 0 & \cdots & 0 \\ 0 & 0 & G_{2_3} & \cdots & 0 \\ \vdots & \vdots & \vdots & \ddots & \vdots \\ 0 & 0 & 0 & \cdots & G_{2_m} \end{bmatrix} \right)$$

Figure 9A:
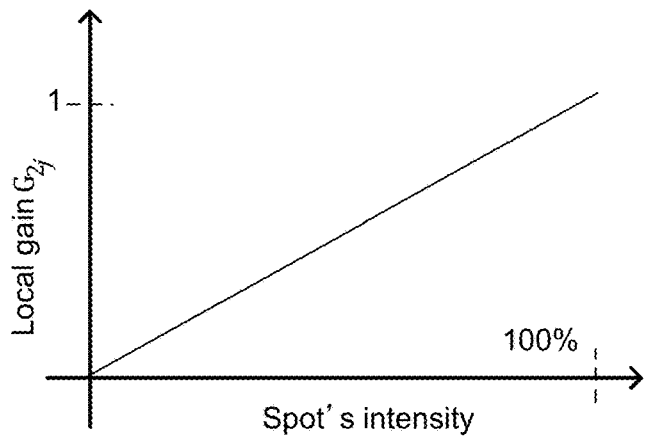
FIGS. 9A-C are illustrations of calculation methods.
Figure 9B:
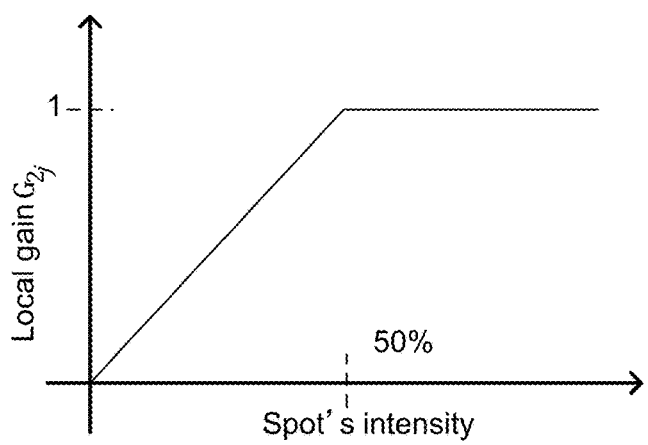
Figure 9C:
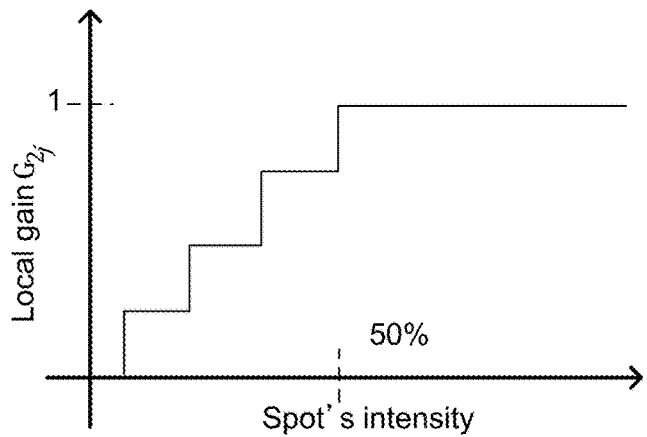

The value $G_{2_j}$ is determined by the quality metric (confidence indicator) of the displacement information such as one or more of: an illumination intensity associated with each spot; a size of each spot; and a signal to noise ratio (S/N) associated with each spot. Each quality metric or confidence indicator is an example of status measurement data that can be used to indicate the quality of the data that is then used to calculate the shape of the wavefront. Many methods may be used for calculating $G_{2_j}$ based on one or more quality metrics such as the one listed above or other quality metrics. FIGS. 9A-C are examples of the calculation methods. The X axis of the graphs in FIGS. 9A-C represents the relative intensity $I_j$ of each spot relative to the saturation value $I_{maximum}$ of the CCD sensor. The Y axis represents a local gain value $G_{2_j}$ for each spot. Equation (7) is an illustration of how $G_{2_j}$ may be described in terms of a transformation function $f$ that is dependent upon one or more of the quality metrics such as the intensity $I_j$ of each spot. FIG. 9A is an illustration in which the transformation function $f$ is a linear function as described by equation (7A). FIG. 9B is also an illustration of a simple linear function $f$ described by equation (7B), but it saturates at 50% (or some other value) of the because 50% of the saturation value may provide a high enough quality signal such that there is high confidence in the quality of the displacement calculation. FIG. 9C is an illustration in which the $G_{2_j}$ may be calculated using look up table such that the transformation function $f$ is a staircase function. Equation (7C) is an example of such a look up table. The intensity $I_j$ may be the peak intensity of the spot j or the mean intensity of the spot j. The transformation function $f$ may be a function other quality metrics instead of the intensity $I_j$ such as the diameter of the spot j; a shape of spot j; or S/N associated with each spot j. The transformation function $f$ may also be a function of multiple quality metrics.

$$G_{2_j} = f(I_j) \quad (7)$$

$$G_{2_j} = f(I_j) = \frac{I_j}{I_{maximum}} \quad (7A)$$

$$G_{2_j} = f(I_j) = \begin{cases} 1 & \text{if } I_j > \frac{I_{maximum}}{2} \\ \frac{2I_j}{I_{maximum}} & \text{if } I_j \leq \frac{I_{maximum}}{2} \end{cases} \quad (7B)$$

-continued

| $\dfrac{I_j}{I_{maximum}}$ | $G_{2_j} = f(I_j)$ |
|---|---|
| 0-10% | 0 |
| 0-20% | 0.2 |
| 0-30% | 0.5 |
| 0-50% | 0.8 |
| 50-100% | 1 |

(7C)

The wavefront sensor 115 of the ophthalmoscope 100 produces a set of wavefront data. The wavefront data includes a plurality of wavefront elements. Each wavefront element among the plurality of wavefront elements is associated with a particular area of a received beam of light received from a fundus 111 being imaged by the ophthalmoscope 100. Each wavefront element includes a plurality of components. Each component among the wavefront element represents a piece of information about the shape of the wavefront received from the fundus 111. A first component of the wavefront element is wavefront shape measurement data. The wavefront shape measurement data may be one or more values that represent a shape of the wavefront in a particular area of the received beam of light. Alternatively, the wavefront shape measurement data may be one or more values that are used to calculate the shape of the wavefront the particular area of the received beam of light. A second component of the wavefront element is status measurement data. The status measurement data is a confidence indicator of ability of the wavefront shape measurement data to represent the shape of the wavefront of the received beam of light in the particular area of the received beam of light with a particular level of accuracy. The status measurement data represents information that is correlated with the accuracy with which the wavefront sensor 115 represents the shape of the wavefront. The intensity of a Hartmann spot is an example of status measurement data. The processor 224 receives the set of wavefront data from the as one chunk of data or as ophthalmoscope 100 or as a plurality of chunks of data. The processor 224 may also receive wavefront data from the ophthalmoscope 100 which it then transforms into the wavefront shape data and status measurement data.

Equation (8) is substantially similar to equation (6) and includes the additional use of a matrix $G_3$ instead of matrix $G_2$ which may be used to represent the local gain associated with each spot. The matrix $G_3$ may be a diagonal matrix with n local gain elements $G_{3_3}$ associated with each actuator i or pixel i.

$$x = G_1(Bs)G_3 \qquad (8)$$

$$\begin{bmatrix} x_1 \\ x_2 \\ x_3 \\ \vdots \\ x_n \end{bmatrix} = \left( G_1 \begin{bmatrix} B_{1,1} & B_{1,2} & B_{1,3} & \cdots & B_{1,m} \\ B_{2,1} & B_{2,2} & B_{2,3} & \cdots & B_{2,m} \\ B_{3,1} & B_{3,2} & B_{3,3} & \cdots & B_{3,m} \\ \cdots & \cdots & \cdots & \ddots & \cdots \\ B_{n,1} & B_{n,2} & B_{n,3} & \cdots & B_{n,m} \end{bmatrix} \begin{bmatrix} s_1 \\ s_2 \\ s_3 \\ \vdots \\ s_m \end{bmatrix} \right) \begin{bmatrix} G_{3_1} & 0 & 0 & \cdots & 0 \\ 0 & G_{3_2} & 0 & \cdots & 0 \\ 0 & 0 & G_{3_3} & \cdots & 0 \\ \vdots & \vdots & \vdots & \ddots & \vdots \\ 0 & 0 & 0 & \cdots & G_{3_n} \end{bmatrix}$$

Figure 6H:
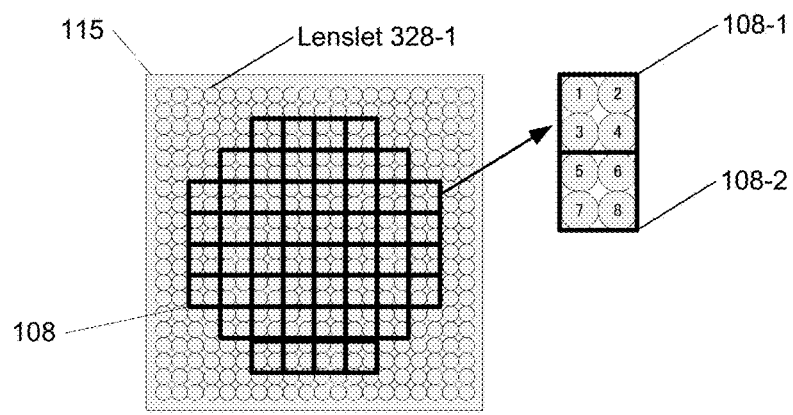
FIG. 6H is an illustration of the spatial correspondence of a wavefront sensor and wavefront adjustment device.

FIG. 6H is an illustration of a wavefront sensor 115 overlay with an illustration of the wavefront correction device 108. The wavefront sensor 115 and the wavefront correction device 108 are not co-located with each other but they are located at optically conjugate planes within the ophthalmoscope 100 as illustrated in FIG. 1. FIG. 6H is an illustration of how an internal components of the wavefront sensor 115 and internal components of the wavefront correction device 108 are correlated with each on their corresponding conjugate planes.

In the example illustrated in FIG. 6H the wavefront sensor 115 is a Shack-Hartmann Sensor, this is a non-limiting example. FIG. 6H illustrates the relative positions of each lenslet 328-1 as a circle. Each lenslet 328-1 produces a spot on the CCD 330. The relative displacement of each spot as detected by the CCD 330 is used to calculate the shape of the wavefront.

In the example illustrated in FIG. 6H the wavefront correction device 108 is a deformable mirror 108, this is a non-limiting example. The deformable mirror 108 includes a plurality of actuators, and a plurality of mirrors (108-1 . . . 108-i . . . 108-n) associated with each actuator. The border of each mirror 108-i is illustrated as a square with a thick black line. As illustrated in FIG. 6H a particular mirror 108-1 is associated with particular lenslets 1 through 4 and a particular mirror 108-2 is associated with particular lenslets 5-8.

The deformable mirror may be a segmented mirror or a flexible mirror membrane. Segmented mirrors have limited cross talk so the influence function A and the corresponding command matrix B are simpler, but there are edge effects due to the edges of the mirrors. While flexible mirror membranes do not have edge effects they do have cross talk issues as changing one portion of the mirror effects other portions of the mirror which has an impact on the influence function A and the corresponding command matrix B. FIG. 6H illustrates a situation in which each particular is mirror is well aligned with a particular set of lenslets. This may not always be the case, alternatively, a particular lenslet may be associated with multiple mirrors, such as when an edge of a mirror does not correlate with an edge of a lenslet. In an alternative embodiment, the deformable mirror may be replaced with a spatial phase modulator in which case, the thick black lines illustrate the edges of pixels in the spatial phase modulator.

As illustrated in FIG. 6, each mirror 108-i is associated with a plurality of lenslets. Each actuator i, pixel i, or mirror 108-i is also associated with a local gain element $G_{3_i}$. Each local gain element is calculated based on the spot illumination condition of the lenslets associated with each spot. The spot illumination condition may include one or more values such as the signal strength of the spot; signal to noise ratio of the spot; and the spot size. Other metrics may also be used to represent the spot illumination condition. The method for calculating $G_{3_i}$ may make use of a second transformation function that is substantially similar to the transformation function $f$ described in equation (7). Except that the second transformation function is function of quality metrics associated with multiple spots. The second transformation function may be a summation of the transformation function $f$ of several spots. The second transformation function may be a statistical value associated with the transformation function $f$ of several spots. The second transformation function may be a separate function of one or more quality metrics associated with multiple spots.

For example the mirror 108-1 is associated with lenslets 1-4. Therefore, local gain element $G_{3_1}$ is associated with the spot illumination condition of lenslets 1-4. Likewise, local gain element $G_{3_2}$ is associated with the spot illumination condition of lenslets 5-8, since mirror 108-2 is associated with lenslets 5-8 as illustrated in FIG. 6H. As each local gain element $G_{3_j}$ is calculated based on metrics which reflect the states of all of the spots formed by the lenslets associated with each local gain element.

Adaptive Optics (AO) Control Method

An embodiment may include an AO control method, non-transitory medium encoded with instructions for performing the AO control method. An embodiment may include one or more processors that perform the method. The one or more processors may include circuits or sets of instructions for performing the AO control method. An embodiment may include a subject inspection apparatus with an AO system that includes the AO control method. An embodiment may include an eye inspection apparatus with an AO system that includes the AO control method.

The AO Control method may include a step of measuring the spot displacement data and outputting the displacement information s. Measuring the spot displacement data may include identifying a set of positions each position will be a spot of light associated with each lenslet. Each position may represent the relative position of the spot of light relative to center associated with a centerline of each lenslet.

The AO control method may also include a step of measuring spot illumination condition associated with each spot. The spot illumination condition may include one more pieces of information that represent the condition of each spot. The AO control method may also include a step of calculating the matrix $G_2$ of local gain values based on the measured spot illumination condition. The spot illumination condition may include one or more values such as the signal strength of the spot; signal to noise ratio of the spot; and the spot size. Other metrics may also be used to represent the spot illumination condition.

The AO control method may also include calculating command values x based on the displacement information s. The AO control method may also include calculating modified command values x based on the displacement information s and local gain $G_2$.

AO Control Flowchart

Figure 7:
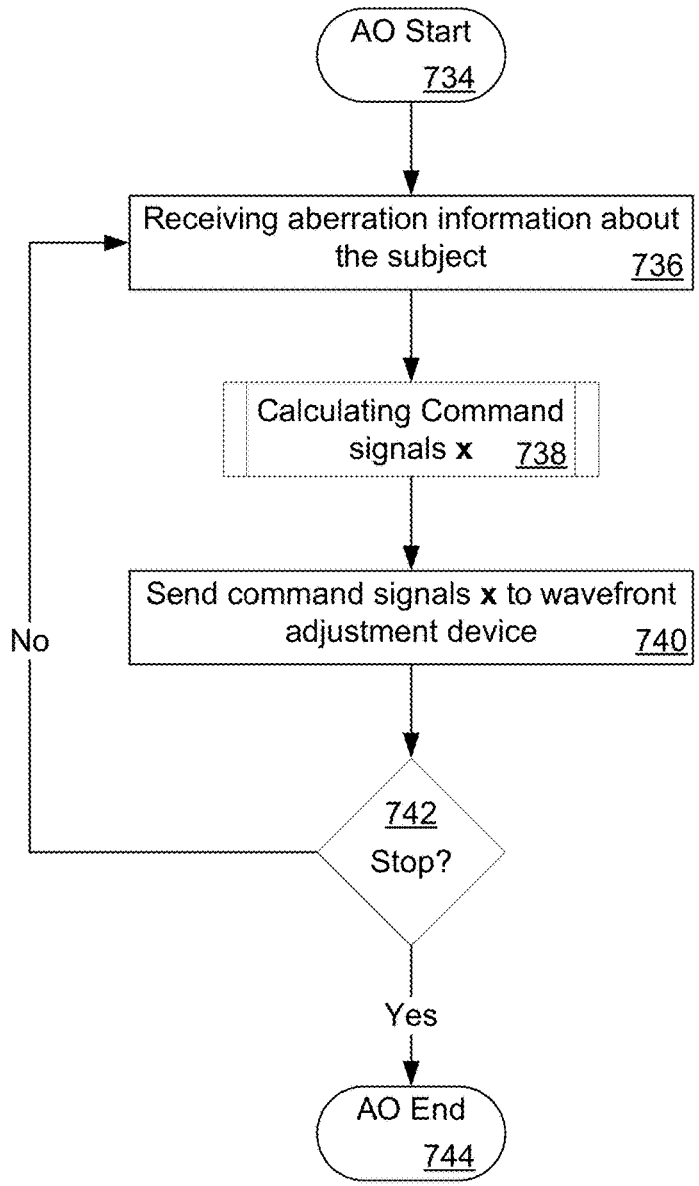
FIG. 7 is an illustration of a method that may be implemented in an embodiment.

FIG. 7 is an illustration of a flowchart 700 that represents how an embodiment of the AO control method may be implemented by one or more processor(s) 224. The processor(s) 224 may be a part of controller 116 and/or a PC 117. The AO control method 700 may include a step 734 of initiating the start of the AO control method. The AO control method may be initiated by a user or may be initiated automatically as part of the startup procedure of an apparatus (e.g. ophthalmoscope 100) that makes use of the AO control method 700. A part of step 734 may include receiving instructions by a processor 224 to imitate the AO control method and may including loading instructions and data into memory 226 associated with the controller 116 and/or the PC 117.

The method 700 may include a step 736 of the processor 224 receiving aberration information about the subject, which may be an eye 111. The aberration information may be received from the wavefront sensor 115. The method 700 may include a step 738 of calculating the command values x. The details of how the command values may be calculated are described in the methods bellow. The command values x may be calculated by the processor(s) 224.

The method 700 may include a step 740 of sending the command values x to the wavefront adjustment device 108. The wavefront adjustment device 108 then adjusts the wavefront to compensate for the measured aberrations. The command values x may take the form of an adjustment value that is applied to each mirror of a deformable mirror or a pixel of each spatial phase modulator. In an alternative embodiment, the command values x may take the form of higher level descriptions of the aberration that needs to be compensated for such as Zernike coefficients for example.

The method 700 may include a step 742 of checking to see if AO control method 700 should be stopped. If the AO control method 700 is not to be stopped, then the AO control method 700 moves back to step 736. If the control method 700 is to be stopped, then the AO control method moves on to step 744 and the AO control method ends. The command to stop may be received from a user from an input device, via a computer, a control switch, or some other interface. Alternatively, the command to stop may be received as a signal from the instrument being controlled by the AO control method 700.

First Exemplary Method of Calculating Command Values

Figure 8A:
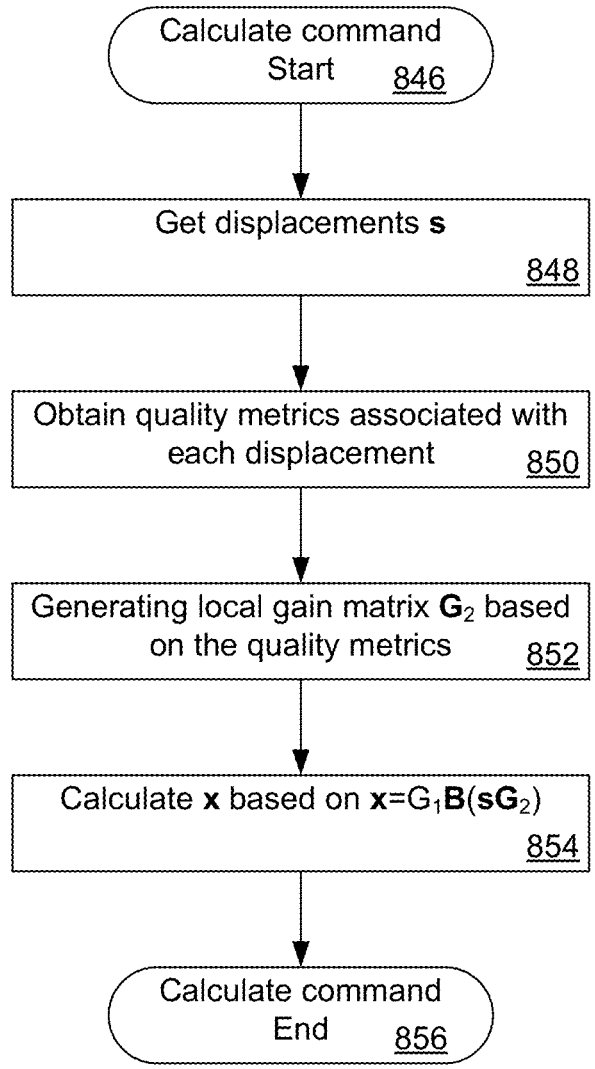
FIGS. 8A-B are illustrations of portions of a method that may be implemented in an embodiment.

The AO control method 700 includes a predefined process 738. The predefined process 738 is a method of calculating command values 738-1. One method of implementing the predefined process 738 is illustrated as method 738-1 in FIG. 8A. The method 738-1 may include the step 846 of starting the method 738-1. The method 738-1 may include the step 848 of obtaining the displacement information s. The method 738-1 may include the step 850 of obtaining information that is indicative of the quality of the displacement information such as one or more of: an illumination intensity associated with each spot; a size of each spot; and a signal to noise ratio (S/N) associated with each spot. The method 738-1 may include a step 852 of generating a local gain matrix $G_2$ based on the information obtained in step 850. For example, each of the local gain elements $G_{2_j}$ of $G_2$ may be calculated in accordance with the intensity of the spot relative to the average value of intensities of all the illuminated spots. This may generate a wide variety of values for the elements in $G_2$. A correction formula such as the following equation (9) may be used to narrow the range of values $$G_{2_{j_{new}}}.$$

Other alternative methods may also be used to adjust the range values for the elements in $G_2$. The method 738-1 may include a step 854 of calculating the command values x based on equation (6). The method 738-1 may end in a step 856. The step 856 may include transmitting command values x from the processor 224 to the wavefront adjustment device 108. Transmitting the command values x may include adding new command values x to old command values x and sending the sum of the old and new values from the processor 224 to the wavefront adjustment device 108.

$$G_{2_{j_{new}}} = \frac{G_{2_j} + \sum_{k=1}^{m} G_{2_k}}{2 \sum_{k=1}^{m} G_{2_k}} \quad (9)$$

Second Exemplary Method of Calculating Command Values

Figure 8B:
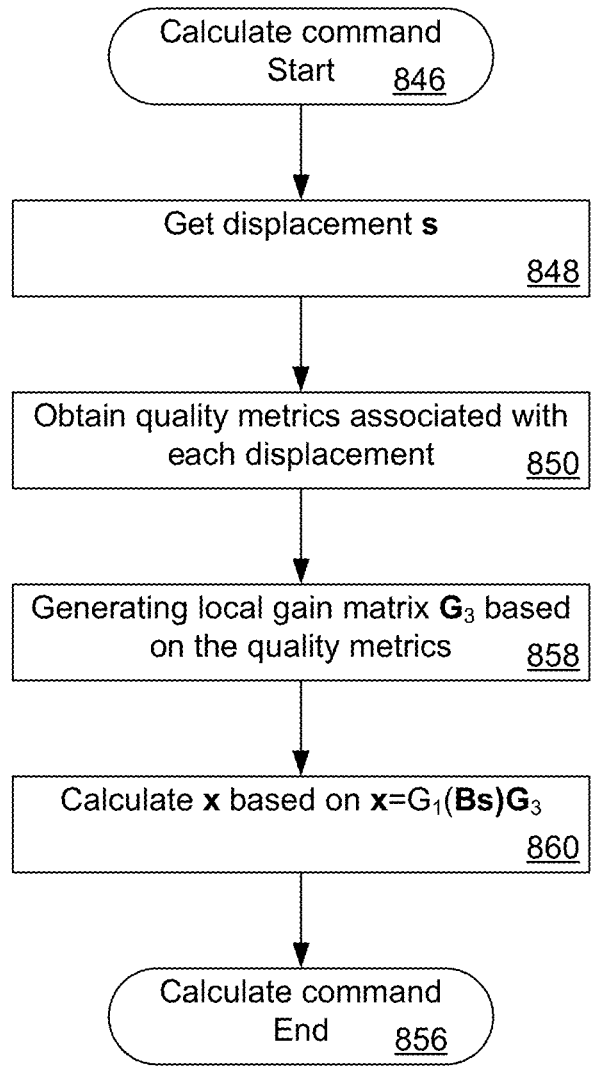

A second exemplary method of implementing the predefined process 738 is illustrated as method 738-2 in FIG. 8B. The method 738-2 includes many of the same steps as method 738-1 including steps 846, 848, 850, and 856. The description of steps 846, 848, 850, and 856 will not be repeated. The method 738-2 may include a step 858 of generating a local gain matrix $G_3$ based on the information obtained in step 850. For example, each of the local gain elements $G_{3_i}$ of $G_3$ may be calculated in accordance with the intensity of the spot relative to the average value of intensities of all illuminated spots. This may generate a wide variety of values for the elements in $G_3$. A correction formula such as the following equation (10) may be used to narrow the range of values $$G_{3_{i_{new}}}$$

similar to equation 8. Other alternative methods may also be used to adjust the range values for the elements in $G_3$. The method 738-2 may include a step 860 of calculating the command values x based on equation (8). The method 738-2 may end in a step 856.

$$G_{3_{i_{new}}} = \frac{G_{3_i} + \sum_{k=1}^{n} G_{3_k}}{2\sum_{k=1}^{n} G_{3_k}} \quad (10)$$

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An ophthalmic apparatus having an adaptive optics system, the apparatus comprising:
    a detecting unit configured to detect each position data of a plurality of spots on a sensor surface and status data of each of the plurality of spots, the plurality of spots being formed on the sensor surface by dividing return light from an eye to be examined by a lens array;
    a calculation unit configured to calculate a set of wavefront data using the each position data and a set of local gain data using the each status data, then obtain a set of a control data based on the set of wavefront data and the set of local gain data; and
    a wavefront adjustment unit configured to adjust the wavefront of the return light based on the set of control data.

2. The apparatus according to claim 1, wherein the status data includes at least one of an intensity associated with each spot; a size of each spot; and a signal to noise ratio (S/N) associated with each spot.

3. The apparatus according to claim 1, further comprising:
    a light sensor unit configured to convert the return light adjusted by the wavefront adjustment unit to an electrical signal; and
    a generating unit configured to generate an image of the eye to be examined based on the electrical signal.

4. The apparatus according to claim 1, wherein the set of local gain data is calculated using a transformation function that is dependent upon the each status data.

5. The apparatus according to claim 1, wherein the apparatus includes an AO-SLO or an AO-OCT.

6. The apparatus according to claim 1, wherein the detecting unit includes a Shack-Hartmann sensor.

7. The apparatus according to claim 1, wherein the wavefront adjustment unit includes a deformable mirror.

8. A method for controlling an ophthalmic apparatus having an adaptive optics system, the method comprising:
    detecting each position data of a plurality of spots on a sensor surface and status data of each of the plurality of spots, the plurality of spots being formed on the sensor surface by dividing return light from an eye to be examined by a lens array;
    calculating a set of wavefront data using the each position data and a set of local gain data using the each status data;
    obtaining a set of a control data based on the set of wavefront data and the set of local gain data; and
    adjusting the wavefront of the return light based on the set of control data.

9. A non-transitory computer readable medium encoded with instructions for a controller to control an ophthalmic apparatus having an adaptive optics system, comprising:
    instructions for detecting each position data of a plurality of spots on a sensor surface and status data of each of the plurality of spots, the plurality of spots being formed on the sensor surface by dividing return light from an eye to be examined by a lens array;
    instructions for calculating a set of wavefront data using the each position data and a set of local gain data using the each status data;
    instructions for obtaining a set of a control data based on the set of wavefront data and the set of local gain data; and
    instructions for adjusting the wavefront of the return light based on the set of control data.

10. An ophthalmic apparatus having an adaptive optics system, the apparatus comprising:
    a detecting unit configured to detect a position of each of a plurality of spots on a sensor surface and a status of each of the plurality of spots, the plurality of spots being formed on the sensor surface by dividing return light from an eye to be examined by a lens array, the status being different from the position;
    an obtaining unit configured to obtain control data based on the position of each of the plurality of spots and the status of each of the plurality of spots; and
    a wavefront adjustment unit configured to adjust a wavefront of the return light based on the control data.

11. The apparatus according to claim 10, wherein the status includes an intensity associated with each spot.

12. The apparatus according to claim 10, wherein the status includes a size and/or a shape of each spot.

13. The apparatus according to claim 10, wherein the status includes a signal to noise ratio (S/N) associated with each spot.

14. The apparatus according to claim 10, wherein the position includes a displacement amount of each spot.

15. The apparatus according to claim 10, further comprising:

a light sensor unit configured to convert the return light adjusted by the wavefront adjustment unit to an electrical signal; and a generating unit configured to generate an image of the eye to be examined based on the electrical signal.

16. The apparatus according to claim 10, wherein each of driving components of the wavefront adjustment unit corresponds to spots of the plurality of the spots, and the obtaining unit obtains the control data based on local gain data calculated by using the each status in unit of the each component.

17. The apparatus according to claim 10, wherein the position, the status and the control data include a matrix form.

18. A method for controlling an ophthalmic apparatus having an adaptive optics system, the method comprising:

detecting a position of each of a plurality of spots on a sensor surface and a status of each of the plurality of spots, the plurality of spots being formed on the sensor surface by dividing return light from an eye to be examined by a lens array, the status being different from the position;

obtaining control data based on the position of each of the plurality of spots and the status of each of the plurality of spots; and adjusting a wavefront of the return light based on the control data.

* * * * *